United States Patent [19]

Antonini

[11] 3,959,249

[45] May 25, 1976

[54] METHOD FOR ISOLATING TRANSFERRINES FROM BIOLOGICAL MATERIALS

[75] Inventor: Eraldo Antonini, Rome, Italy

[73] Assignee: Officina Terapeutica Italiana O.T.I. Laboratorio Biologico S.p.A., Parma, Italy

[22] Filed: Oct. 24, 1974

[21] Appl. No.: 517,742

[30] Foreign Application Priority Data

Oct. 31, 1973 Italy .................................. 30771/73

[52] U.S. Cl. ............................ 260/122; 260/121
[51] Int. Cl.² ...................... A23J 1/06; C07G 7/00; C07G 7/04
[58] Field of Search ........................... 260/122, 121

[56] References Cited
UNITED STATES PATENTS

| | | | |
|---|---|---|---|
| 2,710,858 | 6/1955 | Block et al. ........................ | 260/122 |
| 2,826,571 | 3/1958 | Henika et al. ...................... | 260/122 |
| 3,234,199 | 2/1966 | Reid ................................. | 260/122 |

OTHER PUBLICATIONS

Neurath—The Proteins (2nd ed.), (Vol. 3), (Academic Press), (N.Y.), (1965), pp. 212–213.
Laurell—Chem. Abs. 48, 12831b, (1954).
Blanquet et al.—Chem. Abs. 72, 51678w, (1970).

*Primary Examiner*—Lewis T. Jacobs
*Assistant Examiner*—H. H. Fletcher

[57] ABSTRACT

A method for isolating conalbumin as used for strongly interbinding metals, such as iron and copper. According to the method, the white of egg is caused to pass through chelating ions coordinated to metal ions of the transition group at a pH buffered between 3 and 6. Then the mass is caused to pass through an active component for the conalbumin-metal complex, the conalbumin being finally isolated therefrom.

11 Claims, No Drawings

METHOD FOR ISOLATING TRANSFERRINES FROM BIOLOGICAL MATERIALS

This invention relates to a method for isolating pure transferrines, particularly conalbumin, from biological materials.

It is well known that many biological liquids, such as blood serum, milk, white of egg and the like, contain proteins which are similar to one another, commonly referred to as transferrines, exhibiting the capability of strongly binding certain metals, such as iron and copper.

It is also well known that the white of egg contains remarkable amounts of a transferrine, commonly referred to as conalbumin. The isolation at a natural state of large amounts of pure conalbumin is highly beneficial for all of the possible industrial applications of protein and any research purpose wherein such a protein might be required.

As heretofore known, the methods for isolating transferrines, particularly conalbumin from the white of egg, were based on fractional precipitation with organic solvents or salts and/or chromatography on ion-exchange resins. These known methods involve such disadvantages as those of requiring many passages, substantial time-consuming and rather expensive equipments and reactants.

It is the primary object of the present invention to provide a method enabling to isolate transferrines from biological materials, particularly conalbumin, at a high degree of purity and minimized number of passages.

It is another object of the invention to provide a method for isolating transferrines, method which can be carried out in a very short time, through very easy procedures at room temperature and minimized equipments over those being required when using prior art methods.

These and still further objects are achieved by a method which is characterized in that a biological material is brought to a pH between 3 and 6 and caused to pass through a mass of material comprising a solid support or carrier, the latter containing chelating groups, coordinated to metal ions of the transition group, in the presence of a buffer solution at pH between 3 and 6 which is free of chelating properties, that a solution containing an active component for the transferrine-metal complex is caused to pass through such a mass, and that pure transferrine is separated from the solution which has passed through the mass by removing those components having a lower molecular weight than that of the transferrine.

In order that the method for isolating transferrines from biological materials be more clearly understood, two exemplary embodiments of the method will now be particularly described, while mentioning embodiments for further variants to the method.

EXAMPLE I

Firstly, a $Fe^{+++}$-carboxymethylcellulose complex was prepared.

In order to prepare the above complex, 1.5 kg carboxymethyl cellulose (of preswollen microgranular Whatman CM-52 type) were dispersed in distilled water, treated with 4–5 volumes (about 10 liters) of 0.5 M $FeCl_3$ aqueous solution and stirred for 4 hours. The Fe-CMC (iron-carboxymethylcellulose) complex was then filtered on Buchner and the resin layer washed with distilled water to disappearance of the reaction of $Fe^{+++}$ ions in the filtrate.

Then, the resin was poured into a suitable vessel and treated with 4–5 volumes 1 M $NH_4OH$ (about 8 liters), stirring for 4 hours. The mass was filtered on Buchner and then washed with distilled water until the filtrate had a pH between 7 and 8. The resin was then poured into a suitable vessel and treated under stirring for at least 30 minutes with 3–4 volumes 0.1 M acetate buffer, pH = 5, adjusting pH to 5, if required.

10 kg egg albumin (integral white of egg) were deionized by means of mixed cationic-anionic ion-exchange resins (batch stirring).

The albumin thus deionized was reflux filtered on gauze, the filtrate adjusted to pH = 5 and again reflux filtered by paper-fold filter. The pH of the completely clear obtained filtrate was again checked (its pH should be kept to 5), again adjusted if required, then added with 1/10 of its volume with 0.1 M acetate buffer, pH = 5, and stirred for few minutes. The liquid thus obtained was caused to pass through the Fe-CMC resin, previously prepared as herein described, layered on suitable Buchner provided with a proper filtering card. The gradual adsorption of conalbumin can be visually followed by the progress of a light hazel-brown on the originally dark brown layer of Fe-CMC. Upon completion of the liquid passage, the product was washed with 0.1 M acetate buffer, pH = 5, to disappearance of proteins in the filtrate, then conalbumin was eluted using as an eluent 0.1 M acetate buffer, pH = 5.5, containing $2 \times 10^{-3}$ sodium citrate (0.2 ml 1 M sodium citrate in 100 ml 0.1 M acetate buffer at pH = 5.5).

The conalbumin solution thus obtained was subjected to deferrization by any known method, for example by bringing it to pH = 4.7 with solid citric acid and then repeatedly treating under batch stirring with strong cationic resins, such as those commercially known under trade mark Dowex IX-2 (Cl) or IRA-400 (Cl), each time for about 25–30 minutes and each time filtering and controlling the constancy of pH to the rate of 4.7. The deferrized liquid, brought to pH = 6.5 with concentrated NaOH, was subjected to dialysis in cold distilled water (3°–4°C) with frequent changes of the dialyzing liquid for at least 48 hours. The dialyzate, as reflux filtered on paper, was subjected to lyophilization. The product obtained was subjected to spectrophotometric checks (at 278 millimicrons in the ultraviolet in 0.02 HCl and at 470 and 400 millimicrons in the visible spectrum as Fe-conalbumin) and to electrophoretic checks and resulted to be essentially pure apoconalbumin.

The yield was about 10 g conalbumin per kg albumen.

The lyophilized apoconalbumin resulted to maintain unchanged properties for at least 6 months when stored at room temperature or less. Inter alia, the properties found after storage are as follows:

a. Capability of binding ferric ions in stoichiometric amounts.
b. Mobility in electrophoresis on gel.
c. Capability of inhibiting bacterial growth.

EXAMPLE II

Firstly, a Fe-carboxymethylcellulose complex was prepared: to this end, 50 g carboxymethyl cellulose as commonly used in chromatography (preswollen, Whatman C M 52) were suspended in 250 ml 1M $FeCl_3$ and the suspension was stirred for 3 hours. The resin was then collected on filter and washed with water to removal of excess $Fe^{+++}$ ions. The resin was then suspended in 500 ml 1M $NH_4OH$ and left for 12 hours in this medium.

The suspension was then filtered and the resin washed on filter with water to removal of excess $NH_4OH$. Then, the resin was suspended in water and thus cold stored (+5°C).

With the $Fe^{+++}$-CMC resin prepared as previously described, cromatography columns were provided, having a diameter of 0.7 cm and containing 15 ml of the packed suspension. The column was then balanced with buffer solution comprising 0.05 M buffer at pH = 5.5.

A solution containing about 50 mg conalbumin and having pH = 5.5 and molarity = 0.05 M was applied to the column. The column was then washed with the same buffer as used for the previous balancing.

The eluate was collected in fractions of 2 ml. The optical density of the fractions at 280 millimicrons was determined; then, solid sodium bicarbonate (final concentration about 0.2 M) was added to the fractions and the optical density at 470 millimicrons was determined. By these operations, the protein and conalbumin contents for the column eluate fractions were measured.

The eluate, as obtained with 0.05 acetate buffer at pH = 5.5, contained further proteins, but negligible amounts of conalbumin.

The elution was then continued with 0.05 M sodium borate buffer at pH = 9.2. This second eluate thus obtained contained conalbumin essentially purified from all of the other proteins initially present in the starting material.

A great deal of tests were carried out by varying the above mentioned experimental conditions. The results of these tests were as follows:

When the material containing conalbumin or apoconalbumin was applied to the column balanced with buffers, such as potassium phosphate, at pH higher than 7 and molarity between 0.05–0.2 M, and eluted with the same buffer, the conalbumin was not retained by the column and came out adjacent the elution front.

On the other hand, should the buffer by which the column was balanced and eluted have a pH between 3 and 6 and molarity between 0.01 and 0.2 M, both the conalbumin and apoconalbumin were adsorbed and retained on the column.

The adsorbed conalbumin can be eluted from the column by varying the washing liquid. This can be a buffer at pH higher than 6 (molarity between 0.1 and 0.2 M). The elution of the proteins should be also obtained with a buffer at pH lower than 6, but containing sodium citrate at a concentration of $10^{-3}$M or higher.

After conalbumin elution, the column can be again balanced with the prior buffer and the adsorption and elution process can be repeated with the same previously used resin.

It should be noted that:

a. The conalbumin adsorption on the column under the above described conditions is highly specific. By electrophoresis on gel, it can be shown that other proteins (such as those present in the raw starting material) are not adsorbed and that the protein as adsorbed and then eluted from the column consists of pure conalbumin.

b. In the passage through the $Fe^{+++}$-carboxymethylcellulose column, any apoconalbumin present in the raw starting material is converted to conalbumin, that is the protein as eluted from the column is always the complex of conalbumin with iron.

c. The resin capability of adsorbing conalbumin under the above described conditions specifically depends on the presence of the metal bound to carboxymethyl cellulose. Thus, a column of carboxymethyl cellulose not containing any iron and balanced with acetate buffer at pH 5.5 0.1 M does not significantly retain conalbumin, unlike a column of $Fe^{+++}$-carboxymethyl cellulose under the same conditions.

d. When the above described conalbumin adsorption and elution process is applied to impure chemical compounds or preparations or directly to the white of egg, substantially pure conalbumin is obtained.

The principle of the method for isolating transferrines, as herein above described, is based on the specific property, particularly for conalbumin, of binding to organic and inorganic chelatings of iron, copper and other metals in the transition group. Should the chelating groups be bound to a structure insoluble in aqueous solvents, in the presence of a metal of the transition group the transferrines would remain adsorbed on the solid matrix, while any other proteins present in the biological starting material have no tendency to interact with the metal-solid chelating matrix complex. The elution of the transferrines from the solid matrix can be obtained by exposing the system to solutions having pH and ionic strength other than the initial ones or solutions containing a free chelating in solution and at sufficient concentrations, which can be in the case experimentally determined. The adsorption and elution process for the transferrines from the solid chelating matrix-metal structure can be conveniently carried out by employing such columns as those commonly used in chromatographic methods.

The material on which the transferrines are adsorbed can be prepared by any polymeric material unsoluble in aqueous solvents containing groups, such as carboxylic groups, capable of chelating metal ions of the transition group, such as ferric or rameic ions. A suitable material for its commercial availability is carboxymethyl cellulose in the form as commonly used for chromatography.

The solid chelating matrix is saturated with ferric ions or ions of other metals of the transition group according to commonly known processes. The presence of ferric ions or ions of other metals of the transition group in the solid matrix is essential for the adsorption of conalumin in accordance with the method herein claimed; under the specific conditions of the present method, such as pH = 5.5 and 0.1 M acetate buffer, no significant adsorption is obtained on carboxymethyl cellulose not containing any metal ions.

The specific adsorption of the transferrines, particularly conalbumin, on carboxymethyl cellulose containing chelated ferric ions is accomplished under the compositonal medium conditions as herein above specified, mainly as to pH. The adsorption is mainly efficient in buffers, such as acetic acid, sodium acetate and the like, having a pH lower than 5.5 and molarity = 0.1 M or less. For the sake of stability, it would be convenient not to expose transferrine to pH lower than 4.0.

The elution of the transferrine from the solid matrix can be accomplished by varying the pH and the ionic strength of the solutions in which the matrix is suspended; most conveniently it could be also accomplished with solutions containing materials suitable to chelate ions of the metals in the transition group, particularly ferric ions, such as solutions containing sodium citrate at a concentration higher than $10^{-3}$M. To a major portion, the transferrines are eluted from the solid matrix as a complex with iron. In order to obtain proteins free of iron, the metal would be removed by one of the well known methods to this purpose.

For practical use, the transferrines and particularly conalbumin can be advantageously lyophilized in order to obtain chemical compounds or preparations capable of maintaining, when stored at room temperature for long periods of time (even several months), unaltered chemical-physical and biological properties.

What I claim is:

1. A method for isolating transferrines at a pure state from biological materials containing transferrines, wherein the biological material is brought to pH between 3 and 6 and caused to pass through a mass of material comprising a solid carrier containing chelating groups coordinated to metal ions of the transition group, in the presence of a buffer solution at pH between 3 and 6 free of chelating properties, wherein such a mass is then caused to be passed through by a solution containing a component showing affinity for the transferrine-metal complex, and wherein from said solution which has passed through the mass the pure transferrine is separated by removal of those components having a molecular weight lower than that of the transferrine.

2. A method for isolating transferrines as set forth in claim 1, wherein the mass of solid material comprises a polymeric resin containing carboxylic groups.

3. A method for isolating transferrines as set forth in claim 1, wherein the metal ion is ferric ion.

4. A method for isolating transferrines as set forth in claim 1, wherein the buffer solution for adsorbing the transferrines on the solid mass comprises acetate buffer having a molarity between 0.01 and 0.2 M.

5. A method for isolating transferrines as set forth in claim 1, wherein the solution used for eluting the transferrines from the solid carrier is a buffer solution having a pH between 6 and 11.

6. A method for isolating transferrines as set forth in claim 1, wherein the solution used for eluting the transferrines from the solid carrier is a buffer solution having a pH between 3 and 6 and containing chelating groups at a concentration higher than $10^{-3}$M.

7. A method for isolating transferrines as set forth in claim 6, wherein the chelating material is sodium citrate.

8. A method for isolating transferrines as set forth in claim 1, wherein prior to being caused to pass through the solid mass, the materials having chelating properties are removed from the biological material.

9. A method for isolating transferrines as set forth in claim 8, wherein said removal of the material having chelating properties from the biological material is accomplished by exposing the material to mixtures of anionic and cationic ion-exchange resins.

10. A method for isolating transferrines as set forth in claim 8, wherein said removal of the materials having chelating properties from the biological material is accomplished by dialysis or other known processes to remove those solutes having a molecular weight lower than 10,000.

11. A method for isolating transferrines as set forth in claim 1, wherein said transferrine is conalbumin.

* * * * *